US012042578B2

(12) United States Patent
Trindade Pereira et al.

(10) Patent No.: US 12,042,578 B2
(45) Date of Patent: Jul. 23, 2024

(54) STIFF AND STRONG HYDROGELS, PRODUCTION METHOD AND USES THEREOF

(71) Applicants: INEB-INSTITUTO DE ENGENHARIA BIOMÉDICA, Oporto (PT); UNIVERSIDADE DO PORTO, Oporto (PT)

(72) Inventors: Andreia Sofia Trindade Pereira, Oporto (PT); Fernão Domingos De Montenegro Baptista Malheiro De Magalhães, Oporto (PT); Inês De Castro Gonçalves De Almada Lobo, Oporto (PT)

(73) Assignees: INEB-INSTITUTO DE ENGENHARIA BIOMÉDICA, Oporto (PT); UNIVERSIDADE DO PORTO, Oporto (PT)

( * ) Notice: Subject to any disclaimer, the term of this patent is extended or adjusted under 35 U.S.C. 154(b) by 21 days.

(21) Appl. No.: 17/047,304

(22) PCT Filed: Apr. 10, 2019

(86) PCT No.: PCT/EP2019/059168
§ 371 (c)(1),
(2) Date: Oct. 13, 2020

(87) PCT Pub. No.: WO2019/197504
PCT Pub. Date: Oct. 17, 2019

(65) Prior Publication Data
US 2022/0023504 A1   Jan. 27, 2022

(30) Foreign Application Priority Data

Apr. 11, 2018  (PT) .......................... 110678

(51) Int. Cl.
| | | |
|---|---|---|
| *A61L 27/52* | (2006.01) | |
| *A61L 27/44* | (2006.01) | |
| *A61L 27/54* | (2006.01) | |
| *A61L 29/12* | (2006.01) | |
| *A61L 29/14* | (2006.01) | |
| *A61L 29/16* | (2006.01) | |
| *A61L 31/12* | (2006.01) | |
| *A61L 31/14* | (2006.01) | |
| *A61L 31/16* | (2006.01) | |

(52) U.S. Cl.
CPC .............. *A61L 27/52* (2013.01); *A61L 27/443* (2013.01); *A61L 27/54* (2013.01); *A61L 29/126* (2013.01); *A61L 29/145* (2013.01); *A61L 29/16* (2013.01); *A61L 31/126* (2013.01); *A61L 31/145* (2013.01); *A61L 31/16* (2013.01); *A61L 2300/404* (2013.01); *A61L 2300/406* (2013.01); *A61L 2300/41* (2013.01); *A61L 2300/414* (2013.01); *A61L 2300/442* (2013.01); *A61L 2430/06* (2013.01); *A61L 2430/20* (2013.01); *A61L 2430/26* (2013.01); *A61L 2430/38* (2013.01)

(58) Field of Classification Search
CPC .... C08K 3/042; C08K 5/11; C08K 2201/005; C08F 220/20
See application file for complete search history.

(56) References Cited

U.S. PATENT DOCUMENTS

| | | | | |
|---|---|---|---|---|
| 4,575,539 A | * | 3/1986 | DeCrosta .............. | C08F 265/06 525/283 |
| 2013/0236715 A1 | * | 9/2013 | Zhamu ..................... | H01B 1/04 977/734 |

FOREIGN PATENT DOCUMENTS

| | | |
|---|---|---|
| CN | 103272239 A | 9/2013 |
| CN | 105462142 A | 4/2016 |
| JP | 2013079348 A | 5/2013 |
| WO | WO 2005034852 A2 | 4/2005 |
| WO | WO 2017059322 A1 | 4/2017 |
| WO | WO 2018008474 A1 | 1/2018 |

OTHER PUBLICATIONS

Paul, Arghya, et al., ACSNano.org, vol. 8., No. 8 (2014), pp. 8050-8062 (Year: 2014).*
Chen, Ji et al., Chem. Sci., 2016, 7, 1874 (Year: 2016).*
Patelis, Nikolaos, et al., Front. Surg. (2017) 4:25 (Year: 2017).*
Alam A et al. "Polymer composite hydrogels containing carbon nanomaterials—Morphology and mechanical and functional performance", Progress in Polymer Science, 2017.
Goncalves IC et al."Protein adsorption and clotting time of pHEMA hydrogels modified with C18 ligands to adsorb albumin selectively and reversibly", Biomaterials, vol. 30, 2009, pp. 5541-5551.
Papageorgiou DG et al. "Mechanical properties of graphene and graphene-based nanocomposites", Progress in Materials Science, vol. 90, 2017, pp. 75.
Y.S. Zhang et al. "Advances in engineering hydrogels", Science, vol. 356, No. 6337, 2017.

(Continued)

*Primary Examiner* — Andrew S Rosenthal
*Assistant Examiner* — Lyndsey M Beckhardt
(74) *Attorney, Agent, or Firm* — Leason Ellis LLP

(57) ABSTRACT

The present disclosure relates to the development of hydrogels with extreme stiffness and high-strength. In particular, an hydrogel comprising poly(2-hydroxyethyl methacrylate) and graphene material with a specific oxidation degree. The hydrogels of the present disclosure may be used in medicine, veterinary or cosmetic, namely as scaffold, cartilage, intervertebral disc and blood contact device such as: catheters, vascular grafts, heart valves, stents, artificial kidneys, artificial lungs, ventricular assist devices or drug delivery system. Uses in other areas can be envisaged, like in soft robotics, packaging, sealing and sensors.

9 Claims, 10 Drawing Sheets

(56) References Cited

OTHER PUBLICATIONS

Pinto Artur M et al, "Smaller particle size and higher oxidation improves biocompatibility of graphene-based materials", Carbon, Elsevier, Oxford, GB, vol. 99,,Dec. 15, 2015 p. 318-329.
Bat, E., Hydroxyethyl Methacrylate-based Nanocomposite Hydrogels with Tunable Pore Architecture, JOTCSA, vol. 3, issue 3, pp. 607-622. 2016.

* cited by examiner

STIFF AND STRONG HYDROGELS, PRODUCTION METHOD AND USES THEREOF

CROSS-REFERENCE TO RELATED APPLICATIONS

This application is a U.S. National Stage Application under 35 U.S.C. § 371 of International Patent Application No. PCT/EP2019/059168, filed Apr. 10, 2019, which claims priority to Portugal Patent Application No. 110678, filed Apr. 11, 2018, the contents of which are each hereby incorporated by reference in their respective entireties.

TECHNICAL FIELD

The present disclosure relates to the development of hydrogels with extreme stiffness and high-strength. In particular, an hydrogel comprising poly(2-hydroxyethyl methacrylate) (pHEMA) and graphene material (GM) with a specific oxidation degree.

The hydrogels of the present disclosure may be used in medicine, veterinary or cosmetic, namely as scaffold, cartilage, intervertebral disc and blood contact device such as: catheters, vascular grafts, heart valves, stents, artificial kidneys, artificial lungs, ventricular assist devices or drug delivery system. Uses in other areas can be envisaged, like in soft robotics, packaging, sealing and sensors.

BACKGROUND

Hydrogels are hydrophilic polymer networks capable of absorbing large amounts of water. This swelling capacity allows applications in tissue engineering, drug delivery, coating of medical devices, removal of dyes and heavy metals, industrial plantations and biosensors[1]. However, poor mechanical properties have limited their widespread use in load bearing applications[1]. To surpass this limitation, several approaches have been proposed: use of higher amounts of crosslinking agent, brittle/ductile inter-penetrating networks (double-network hydrogels), nanofillers, and nanostructured hydrogels[1]. However, these often lead to loss of key features, like swelling capacity, hemo/biocompatibility and non-fouling characteristics, and/or to difficulties in preparation. Design and production of strong hydrogels are a central issue in the materials science field which limits their application in several load bearing applications.

Moreover, designing biomaterials with long-term stability in the body and that mimic the biomechanical properties of native tissues for cartilage and intervertebral disc replacement still remains a challenge. Also, the limited performance of currently available blood-contacting materials has been a gap in the biomedical field that has high impact on the quality of life and survival of patients and also in worldwide economy. Blood, a body fluid constituted by water, plasma proteins, red and white blood cells and platelets, is usually confined to the vascular system. As soon as a biomaterial contacts with blood, the plasma proteins adsorb to the biomaterial surface promoting the recruitment, activation and adhesion of platelets. Activation of the coagulation cascade leads to higher adhesion of platelets followed by formation of a fibrin clot which culminates in thrombus development. Besides thrombus formation, adhered plasma proteins also promote activation of immune cells which can induce an immunologic response against the foreign material. Hemolysis is another episode that conditions the performance of biomaterials after implantation. In spite of several efforts and strategies such as designing of nonfouling and/or anti-thrombogenic surfaces or promotion of endothelization (i.e. vascular grafts, heart valves, stents), there is an urgent need to develop new biomaterials for blood contacting applications.

These facts are disclosed in order to illustrate the technical problem addressed by the present disclosure.

GENERAL DESCRIPTION

Designing hydrogels with high-strength and stiffness remains a challenge, limiting their usage in several applications that involve load bearing[1]. Surprisingly in the present disclosure, through in situ incorporation of graphene oxide (GO) in poly(2-hydroxyethyl methacrylate) (pHEMA), it was created a hydrogel with outstanding stiffness (Young's modulus of 6.5 MPa, 8.5 times higher than neat pHEMA) and tensile resistance (ultimate tensile strength of 1.2 MPa, 7.8 times higher than neat pHEMA). All the measurements were performed with hydrated samples at room temperature (20° C.). For tension, loadings were recorded at a displacement rate of 10 mm/min.
For compression, loadings were recorded at a displacement rate of 60 mm/min.

These tension values of stiffness are comparable to polydimethylsiloxane (PDMS), cartilage and artery walls, while tensile resistance is similar to rigid foams, PDMS and cork. The water absorption capacity, surface wettability and biocompatibility of the hydrogel remain similar to those of neat pHEMA. This new material is an important breakthrough for application of hydrogels in different fields.

In the present disclosure, graphene (G) is a single-layer sheet of $sp^2$-bonded carbon atoms in a two-dimensional (2D) honeycomb lattice. This material was first isolated in 2004 and ever since the number of studies involving the properties and applications of Graphene material (GM) has been exponentially increasing[3]. G has been described as the strongest material in the world making GM appealing fillers for polymers reinforcement[3]. However, the efficiency of GM in the reinforcement of polymers is strongly dependent of the chemical nature of the polymer as well as the oxidation degree, thickness, lateral size and production technique of $GM^3$. GO is a single layer of carbon atoms in $sp^2$ bonds separated by aliphatic 6 membered rings containing hydroxyl, epoxide and carboxylic groups[3]. It has outstanding physicochemical properties, such as stability, high area/thickness ratio and mechanical strength[3].

An aspect of the present disclosure relates to a hydrogel comprising poly(2-hydroxyethyl methacrylate) with at least 1% (w/v) of GM wherein the oxidation degree of the GM is between 10-50% (oxygen atomic percentage), wherein the GM is incorporated in the hydrogel. Surprisingly the developed hydrogel has an extreme stiffness and high-strength (FIG. 3, 6, 7, 9, 18, 19).

In an embodiment for better results, the GM may further comprise an oxidation degree between 20-50% (oxygen atomic percentage), preferably an oxidation degree between 30-35% (oxygen atomic percentage). Surprisingly the developed hydrogel has an extreme stiffness and high-strength (see FIG. 9).

In an embodiment for better results, the GM may be obtained by the modified Hummers' method in the case of oxidized graphene material.

In an embodiment for better results, the GM may be incorporated in powder or in a water dispersion.

In an embodiment for better results, the graphene material is incorporated in the hydrogel.

In an embodiment for better results, the hydrogel of the present disclosure may comprise at least 0.01% (w/v) of GM, preferably at least 1% (w/v) of GM, more preferably at least 2% (w/v) of graphene material.

In an embodiment for better results, the hydrogel may comprise 1-5% (w/v) of GM, preferably 1.1-5% (w/v) of GM, more preferably 1.5-4% (w/v) of GM.

In an embodiment for better results, the hydrogel of the present disclosure may comprise few layers graphene, few layers graphene oxide, multi-layer graphene or multi-layer graphene oxide, preferably comprising 2-25 layers. The number of layers could be determined by x-ray diffraction.

In an embodiment for better results, the multi-layer graphene oxide comprises 2-25 layers, preferably 3-15 layers, more preferably 3-12 layers (see FIG. 9).

In an embodiment, the number of layers may be determined by x-ray diffraction through the Scherrer equation ($\tau=K*\lambda/\beta \cos(\theta)$) and Bragg equation ($\lambda=2d \sin \theta$), where $\tau$ is thickness, K is a dimensionless shape factor (0.89), $\lambda$ is the X-ray wavelength, $\beta$ is the line broadening at half the maximum intensity, $\theta$ is the Bragg angle (which is experimentally measured) and d is inter layer space. Then number of layers (n) are $n=\tau/d$.

In an embodiment for better results, the platelet lateral size varies between 1-30 µm, preferably between 2-20 µm, more preferably 2-4 µm. The platelet lateral size of the layers may be determined by Transition Electron Microscopy, Atomic Force Microscopy or Scanning Electron Microscopy.

In an embodiment for better results, the hydrogel may further comprise a crosslinking agent, preferably tetraethylene glycol dimethacrylate.

In an embodiment for better results, the amount of crosslinking agent varies between 0-10% (w/w), preferably 2-5% (w/w).

In an embodiment for better results, the hydrogel may further comprise a second polymer, an antifouling agent, a surfactant agent, a biomolecule, an antiseptic agent, an anti-inflammatory agent, an antibiotic agent, a therapeutic agent, a pharmaceutical dye, peptides, endothelial factor, growth factor, or mixtures thereof. Preferably, wherein at least one of the previous elements is bound to GM.

In an embodiment for better results, the GM is selected from a list consisting of: graphene, graphene oxide, few-layer graphene, few-layer graphene oxide, multi-layer graphene, multi-layer graphene oxide, or mixtures thereof.

In an embodiment for better results, GM can be incorporated in pHEMA as a water dispersion or a powder. The use of graphene material as a powder allows the incorporation of higher amounts. However, for the same concentration, incorporation of graphene materials as a water dispersion leads to better results (see FIG. 7).

In an embodiment for better results, the hydrogel of the present disclosure may further comprise a second polymer selected from a list consisting of: polycaprolactone, hyaluronic acid, alginate, chitosan, polylactic acid, collagen, silk, polyglicolic acid, poly(ethylene glycol), polyhydroxobutyrate, gelatin methacryloyl, poly vinyl acid, acrylamide, as well as other natural or synthetic polymer, biodegradable or not, or mixtures thereof.

In an embodiment for better results, the hydrogel of the present disclosure may further comprise an antifouling agent, a surfactant agent, an antiseptic agent, an anti-inflammatory agent, an antibiotic agent, a therapeutic agent, a pharmaceutical dye, peptides, endothelial factors, growth factors, or mixtures thereof.

In an embodiment for better results, the hydrogel of the present disclosure may be transparent, brown, grey or black.

Another aspect of the present disclosure is to use the hydrogel of the present subject-matter in medicine, in veterinary or cosmetic.

The hydrogel of the present disclosure may be used in a medical device.

Another aspect of the present disclosure is an article comprising the hydrogel of the present subject-matter. The article may be used for cartilage, intervertebral disc, catheter, vascular graft, heart valve, stent, artificial kidney, artificial lung, ventricular assist devices, contact lenses, keratoprosthesis, scaffold, among other medical devices.

Another aspect of the present disclosure relates to a method for producing bio/hemocompatible non-fouling hydrogels with outstanding stiffness and tensile resistance and improved elasticity. The hydrogel of the present disclosure will pave the way for hydrogels application in several load-bearing applications, namely in the design of tissues where non-adhesive properties are an asset, such as cartilage, intervertebral disc and blood-contact devices.

In the present disclosure, poly(2-hydroxyethyl methacrylate) (pHEMA) is a synthetic hydrogel described as a non-fouling material, pHEMA limits the adsorption of protein, platelets and cells on its surface. Due to its biocompatibility, this material is a Food and Drug Administration (FDA) approved hydrogel already used in the production of contact lenses and keratoprosthesis. Several research works have shown potential application of pHEMA in the design of drug delivery systems, wearable devices to stimulate wound healing and scaffolds for soft tissues. However, the usage of pHEMA as well as other hydrogels in load bearing applications, such as the designing of blood contacting materials is limited due to their wear tensile resistance, which is in the order of few hundred kPa. Thus, pHEMA has only been described as a coating for the development of blood contacting material.

BRIEF DESCRIPTION OF THE DRAWINGS

The following figures provide preferred embodiments for illustrating the disclosure and should not be seen as limiting the scope of invention.

DETAILED DESCRIPTION

Figure 1:
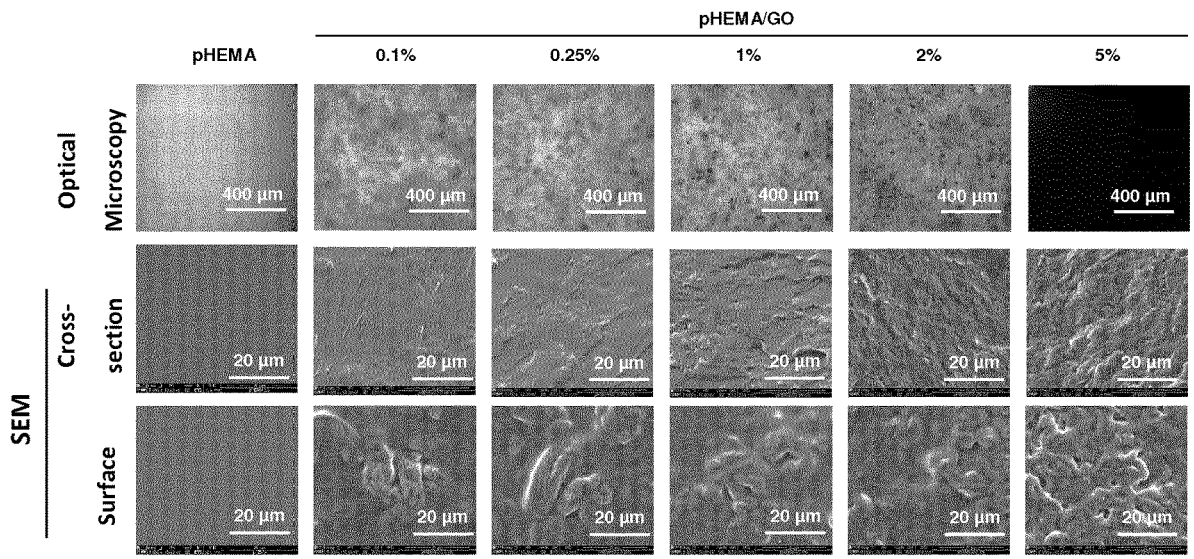
FIG. 1—Optical Microscopy (first line) and SEM images (lines 2 and 3) of pHEMA and pHEMA/GO composites.

The present disclosure relates to develop hydrogels with extreme stiffness and high-strength. In particular, an hydrogel comprising poly(2-hydroxyethyl methacrylate) (pHEMA) and graphene material (GM) with differing lateral size, oxidation degree and thickness.

In the present subject-matter it is also disclosed a new and easy approach to improve the mechanical performance of an FDA approved hydrogel, poly(2-hydroxyethyl methacrylate) (pHEMA), based on incorporation of different GM and varying amounts of graphene oxide (GO). The hydrogels were fabricated by in situ free-radical polymerization of the monomer (2-hydroxyethyl methacrylate) and crosslinking agent (tetraethylene glycol dimethacrylate; TEGDMA) in the presence of different contents of GO (0%, 0.1%, 0.25%, 1%, 2% and 5% (w/v)) or GNP M5, GNP M15, GNP M5ox and GNP M15ox (with 1% (w/v)=1.63 (w/w)) dispersed in water/ethylene glycol solution.

In an embodiment for better results, graphene is few layers sheets (2-12) of $sp^2$-bonded carbon atoms in a two-dimensional (2D) honeycomb lattice, graphene oxide (GO) is a few layers sheets (2-12) of carbon atoms in $sp^2$ bonds separated by aliphatic 6 membered rings containing hydroxyl, epoxide, carbonyl and carboxylic groups, with percentage of oxygen between 10-50%, preferably 30-35%, GNP of grade M purchased from XG Sciences is multi-layer sheets (12-25) carbon atoms in a two-dimensional (2D) honeycomb lattice with surface area of 120-150 $m^2g^{-1}$, the lateral size of these materials is 5 μm (GNP M5) or 15 μM (GNP M15), GNPox are oxidized forms of GNPs, containing 20 up to 50% of oxygen atoms, or mixtures thereof.

pHEMA/GM composites were evaluated regarding polymerization degree (Infrared spectroscopy—FTIR-ATR), GO presence (RAMAN), GM dispersion (optical microscopy and TEM), surface topography (SEM), wettability (contact angle measurements), swelling capacity (gravimetry) and mechanical properties (tensile and compression tests). Biocompatibility was evaluated using mouse fibroblasts (NIH3T3) and endothelial cells (HUVECs) regarding cell adhesion/proliferation by immunofluorescence and cytotoxicity of medium extracts by resazurin assay. Hemocompatibility was assessed regarding hemolytic potential by hemolysis assay and platelets adhesion/activation by SEM.

In an embodiment, the incorporation of GM increases surface roughness of pHEMA, although polymerization, swelling capacity (~50%) and surface wettability (~25° contact angle) are not affected. Regarding the mechanical properties, the presence of non-oxidized GNPs does not influence the performance of neat pHEMA. GO is the most efficient oxidized nanofiller, with incorporation of 5% GO in pHEMA increasing its compressive and tensile stiffness 4× and 8.5× (4 MPa and 6.5 MPa, respectively) and tensile resistance 7.8× (1.2 MPa). This is an outstanding value for tensile resistance since for most of hydrogels described in the literature GO incorporation increases only 2-3×, reaching about 400 kPa. The elasticity of the hydrogel can be improved in 50% using concentrations of up to 2% GO, returning to pHEMA original values when 5% GO is used. Regarding the biological properties, GM incorporation in pHEMA does not promote cell and platelets adhesion at the surface, neither hemolysis nor cytotoxicity.

In an embodiment of the preparation of Graphene Materials (GM), Graphene Nanoplatelets (GNP) of grade M were purchased from XG Sciences (Lansing, MI, USA) with surface area among 120-150 $m^2g^{-1}$, average thickness of 6 nm and an average diameter of 5 μm (GNP M5) or 15 μm (GNP M15). GO, GNP M5ox and GNP M15ox were prepared by oxidation of carbon graphite (purity: ≥99%, diameter: 7-11 μm; purchased from American Elements), GNP M5 or GNP M15, respectively, by modified Hummers method[4]. For this, 3 g of carbon graphite, GNP M5 or GNP M15 were mixed with a $H_2SO_4/H_3PO_4$ (4:1) mixture (150 mL) being cooled to 0° C. using ice bath. After that, 18 g of $KMnO_4$ were gradually added, the mixture kept for 2 h at 35° C. under stirring and afterwards refrigerated to 0° C. and 450 mL of $dH_2O$ added slowly. To eliminate the excess of $KMnO_4$, $H_2O_2$ was added until oxygen release stopped. After overnight resting, the GM were washed by consecutively centrifuging at 4000 rpm during 20 min, until pH of supernatant reached the pH of distilled water. To obtain GO, the suspension was sonicated during 6 hours in ultrasonic bath. GNP M5ox, GNP M15ox and GO suspensions were freeze-dried for 3 days at −80° C. and 0.008 mBar to obtain dry powders.

In an embodiment, the production of the hydrogels of the present disclosure may have the following steps: Poly(2-hydroxyethyl methacrylate) (pHEMA) was produced by in situ polymerization[5], in the absence or presence of GM. 7.5 ml of 2-hydroxyethyl methacrylate monomer (HEMA; >99.5%, Polysciences, no. 04675) were added to a water/ethylene glycol (Sigma Aldrich, no. 9300) mixed solvent (1.5 mL/2.25 mL) with 0%, 0.1%, 0.25%, 1%, 2%, 5% (w/v) of GO or GNP M5, GNP M15, GNP M5ox and GNP M15ox with 1% (w/v). The mixture was vortexed for 30 seconds and sonicated in an ultrasound water bath during 15 min. After that, were added 0.345 mL of tetraethylene glycol dimethacrylate (TEGDMA; Polysciences, no. 02654) crosslinking agent and 1.5 mL of 40% ammonium persulfate (APS; 98%, Aldrich, no. 24,861-4) and 15% sodium metabisulfite (SMB; 97%, Aldrich, no. 25.555-6) as redox initiators to begin the radical polymerization. 2D films or 3D tubes were produced using as moulds two clean glass plates with a 0.54 mm thick teflon or a tube and glass rod with 6 mm and 4 mm of diameter, respectively. After overnight resting, the hydrogels were released from the moulds and rinsed in distilled water for 4 h (water renewed every hour) to leach out initiators, unreacted monomers and oligomer residues. 5% of GO (w/v) was the maximum incorporated in pHEMA due to the high increase in the pHEMA/GO viscosity, before polymerization, which prevented its moulding between the glass plates.

In an embodiment of materials physical-chemical and mechanical characterization, GM was analysed regarding surface chemical composition (and oxidation degree) by X-ray photoelectron spectroscopy (XPS), exfoliation degree by Transmission Electron Microscopy (TEM) and X-ray diffraction (XRD) and platelets morphology by Scanning Electron Microscopy (SEM).

In an embodiment, pHEMA/GM composites were evaluated regarding polymerization degree by Fourier transform infrared spectroscopy with attenuated total reflectance (FTIR-ATR), GO presence by RAMAN, GM dispersion in the polymer by optical microscopy, SEM and TEM, surface topography by SEM, wettability by captive bubble contact angle measurements, swelling capacity by gravimetric analysis and mechanical properties by tensile and compression tests.

In an embodiment of XPS of GM powders, pellets were analysed using a Kratos Axis Ultra HAS (Kratos Analytical, UK) equipment at "Centro de Materiais da Universidade do Porto" (CEMUP, Porto, Portugal). An Al monochromator with 15 kW was used as X-ray source. The survey spectrum of all GM was obtained at 80 eV and the C and O spectra at 40 eV.

In an embodiment, X-ray diffraction (XRD) patterns of the GM powders were measured on a Rigaku SmartLab that operates with 45 kV and 200 mA and a Cu source with a wavelength of λ=1.540593 in a Bragg-Brentano geometry. All the samples were measured in a range of 5 to 60 theta in a rotative system (30° Deg/min).

In an embodiment, all GM powders and pHEMA/GM composites were analyzed by Scanning Electron Microscopy (SEM) FEI QUANTA 400 ESEM (ThermoFischer, USA). Materials were mounted on carbon tape and coated with a thin layer of gold/palladium by sputtering to improve the visualization by SEM.

In an embodiment, TEM images of pHEMA/GM composites were conducted on JEOL JEM 1400 TEM (Tokyo, Japan) coupled to a digital camera CCD Orious 1100 W (Tokyo, Japan) at Histology and Electron Microscopy Service (HEMS, i3S, Porto, Portugal). pHEMA/GM composites were visualized after preparation of ultrathin sections (40-60 nm thickness) using diamond knives in a Leica Reichert SuperNOVA Ultramicrotome.

In an embodiment, FTIR spectra of dehydrated pHEMA/GM composites were assessed using a Perkin Elmer Frontier spectrophotometer coupled to a universal Attenuated Total Reflection (ATR) sampling accessory. Spectra were obtained in duplicate using 100 scans and resolution of 2 $cm^{-1}$. A baseline correction and smooth reduction was performed.

Raman spectra were acquired to evaluate the presence of GO in composites. The spectra were acquired using a confocal Raman microscope, LabRAM HR800 UV, Horiba Jobin-Yvon. The excitation was provided by a 515.2 nm laser with an acquisition time of 30 s. A 50× objective (Olympus) lens with a numerical aperture of 0.55 was used. Measurement were performed using dehydrated samples and at least 5 spectra were acquired for each condition. Spectra were baseline corrected and smoothed.

In an embodiment, inverted drop method was performed with a Data Physics goniometer, model OCA 15 equipped with a video CCD-camera to evaluate the captive-bubble contact angles of hydrated pHEMA/GM composites. For this, the samples were attached individually to a steel slide and placed into a glass chamber with ultrapure water. To measure the contact angle, a 10 μl air bubble was released from a J-shaped needle on the sample's surface being the angle measured using the software SCA.

In an embodiment, pHEMA/GM swelling profile was assessed by gravimetric analysis of dehydrated disc when immersed in water during 4 h. At different time points, 3 replicates of each sample were removed from water, blotted with a kimwipe and weighed. The following equation was used to determinate the swelling degree:

$$\text{Swelling degree}(\%) = \frac{Ws - Wd}{Wd} \times 100$$

where Ws the weight of the swollen polymer and Wd is the weight of the dry polymer. The swelling profile of each material was determined at least 3 times.

In an embodiment, tensile resistance of hydrated pHEMA and pHEMA/GM was evaluated in a Mecmesin Multitest-1d motorized test frame using the testing parameter ASTM D 882-02. Materials were cut (60 mm of length and 15 mm of width) and the loadings recorded at a strain rate of 10 mm/min using a digital dynamometer (10 N or 200 N—Mecmesin BF). For each condition at least 6 samples of 2 different batches of materials were tested.

Compression properties were measured using pHEMA and pHEMA/GO composites discs with cylindrical shape produced as described above using a 24-well as mold (Ø 15.6 mm and v=3.4 mL). Compression was evaluated with a texture analyser (TA-XT2i, Stable Micro Systems) using a load cell of 5 kg and a cylindrical Delrin probe with a 0.5 inch diameter with 126.68 $mm^2$ of area and a displacement rate of 60 mm/min. The compression tests using 20 N load was applied vertically and the strain was measured, being performed in duplicate using 3 replicates.

In an embodiment, to evaluate the blood compatibility of pHEMA/GM composites, materials were incubated with Red Blood Cells (RBCs) to verify their hemolytic potential or with human platelets to evaluate their capacity to induce platelet adhesion and activation. Before the assays, all materials were cut into discs with 9 mm diameter and sterilized in 70% (v/v) ethanol solution followed by rising with phosphate buffered saline (PBS; 0.01M, pH 7.4)).

In an embodiment, Red blood cells (RBCs) were isolated from human buffy coats by differential centrifugation at 400 g during 30 minutes in the presence of Histopaque-1077 (SigmaeAldrich). After centrifugation, the upper layer (containing plasma components and mononuclear cells) was removed from the lower layer (containing the RBCs). After that, the lower layer was washed three times with PBS and the purified RBCs were diluted to a concentration of $2\times10^8$ cells/mL. 300 mL of RBC were incubated during 3 h at 37° C. in 48-well polypropylene plate containing pHEMA/GM films. 48-well plates were centrifuged at 4000 rpm for 15 min and 100 mL of supernatant were collected from each well to black 96 wells polystyrene plates. The absorbance was red at 380, 415, and 450 nm using a micro-plate reader spectrophotometer. The amount of released hemoglobin (Hb) was calculated using the following equation:

$$Hb(mg.dL^{-1}) = \frac{(2 \times A415 - (A380 + A450)) \times 1000}{E}$$

where A415, A380, A450 represent the absorbance values at of samples at 415 nm, 380 nm, 450 nm, respectively, and E the molar absorptivity of oxyhemoglobin at 415 nm.

The hemolytic potential of pHEMA/GM composites was determined according to the following equation:

$$\% \text{Hemolysis} = \frac{Hb \text{ sample}}{\text{total } Hb}$$

where, total Hb is the correspondent value for 100% hemolysis with Triton 1%. The assay was performed with 5 replicates.

In an embodiment, platelet adhesion and activation to pHEMA/GM composites were assessed in vitro using human platelets concentrate (PC). Briefly, 48-well polystyrene plates were blocked to avoid platelet activation by the wells by incubation in a solution of 1% (w/v) bovine serum albumin (BSA) in PBS (1 h; 37° C.) followed by rising with PBS. pHEMA/GM films were pre-immersed in pure human plasma (1 h; 37° C.) and then transferred to the BSA-coated plates, incubated with PC at $3\times10^8$ platelet/mL (1 h; 37° C.; 100 rpm). Afterwards, materials were rinsed with PBS and the adhered platelets fixed with 1.5% v/v glutaraldehyde in 0.14 M sodium cacodylate buffer for 30 min at RT. For samples dehydration, materials were incubated with a growing ethanol/water gradient, 50, 60, 70, 80, 90 and 99% (v/v), for 10 min each. Samples were finally dried by critical point (variation of temperature 4° C. to 33-38° C. maximum pressure of 1000-1400, 5 cycles of 25 min). Adhered platelets were visualized by SEM and evaluated regarding the number of adherent platelets and degree of activation.

In an embodiment, in vivo hemocompatibility of pHEMA/GO hydrogel was evaluated using non-heparinized pigs as animal model. Conduits of pHEMA/GO hydrogel with an inner diameter of 4 mm and an outer diameter of 6 mm were connected to the pig carotid arteries (A-V shunt) being in contact with circulating blood for 1 h. As control, ePTFE conduits were used. After this acute contact, both conduits were perfused with physiological saline solution and divided in two parts for surface lumen evaluation by SEM. For this, the conduits were fixed in 2.5% glutaraldehyde for 2 h, dehydrated in an ethanol/water gradient, 50, 60, 70, 80, 90 and 99% (v/v), for 10 min each, and critical point dried.

In an embodiment, the in vitro biocompatibility of pHEMA/GO composites (0-5% w/v) was evaluated by the incubation of mouse fibroblasts NIH 3T3 with extracts of materials. The extracts were prepared as described in ISO 0993-12:2004. Briefly, materials were cut with Ø=13 mm and sterilized with ethanol 70%. After the sterilization step, materials were rinsed with PBS and extracted with DMEM+ culture medium (Dulbecco's modified Eagle's medium (DMEM, Gibco) supplemented with 10% (v/v) Fetal bovine serum (Gibco) and 1% (v/v) penicillin/streptomycin (biowest)) during 24 h at 37° C. in an orbital shaker at 100 rpm. Cells were seeded in 96-well plates at density of $1\times10^5$ cells/mL and maintained in culture for 24 h in DMEM+. After that, the medium was replaced by material extracts, according to ISO 10993-5:2009(E). After 24 h of incubation at 37° C., mitochondrial metabolic activity of cells was quantified by resazurin assay. Extracts of TCPS discs were used as positive control of cell growth while a solution of DMEM with 1 mM $H_2O_2$ was used as negative control. Assays were performed with n=5 and repeated twice.

In an embodiment, in vitro biocompatibility of pHEMA/GM composites (1% (w/v)) was also evaluated using Human Umbilical Vein Endothelial Cells (HUVECs, Sciencell) regarding cytotoxicity of medium extracts by resazurin assay and cell adhesion/proliferation by immunofluorescence. HUVECs were grown at 37° C. under a 5% $CO_2$ humidified atmosphere, in complete medium (M199+) which consists in M199 medium (Sigma) supplemented with 10% v/v inactivated FBS, 1% v/v Penicillin/Streptomicin (Biowest), 90 µg/mL of heparin (Sigma, H3149) and 15 µg/mL of endothelial cell growth supplement (ECGS, Corning, 354480) in 1% w/v gelatin coated flasks (Sigma). Cells were used until passage 4.

In an embodiment, for evaluation of cytotoxicity, cells were seeded at a density of $1\times10^5$ cells/mL$^1$ in the wells of a 96-well plate previously coated with 1% (w/v) gelatin and incubated during 24 h in M199+. Afterwards, materials extracts were added and incubated during 24 h. Material extracts were prepared as described in ISO 0993-12:2004. Briefly, materials were cut with Ø=13 mm, sterilized with ethanol 70%, rinsed with PBS, incubated with M199 supplemented with FBS (24 h; 37° C.; 100 rpm) and afterwards supplemented with ECGS (15 µg/mL) of heparin 90 µg/mL. Extracts of TCPS discs were used as positive control of cell growth while a solution 1 mM $H_2O_2$ (in complete medium) was used as negative control. Mitochondrial metabolic activity of cells was quantified by resazurin assay, where the relative fluorescence units of supernatant containing 20% (v/v) resazurin incubated for 3 h were measured using a fluorimeter. Assays were performed with n=5 and repeated twice.

To assess the pHEMA/GM composites capacity to induce HUVECs adhesion and proliferation, $1.6\times10^4$ cells (in a volume of 50 µL in complete medium) were seeded on each material (in 48-well polystyrene plates) and incubated for 4 hours. After that, M199+ was added to each material reaching final volume of 300 µL and culture was maintaining during 48 h. Metabolic activity was measured at time points 24 h and 48 h by the resazurin assay as previously described. After 48 h, materials were rinsed with PBS and cells fixed using paraformaldehyde 4% (v/v), stained with DAPI (DNA in nuclei) and Phalloidin (F-actin in cytoskeleton) and observed in inverted fluorescence microscope.

Fourier-transform infrared spectroscopy (FTIR) spectroscopy of pHEMA/GO composites demonstrates that pHEMA polymerization occurred even in presence of GO since the characteristics bands of HEMA monomers, C=C (815 $cm^{-1}$, 943 $cm^{-1}$, 1635 $cm^{-1}$), are not present in any of the spectra. Moreover, spectra of pHEMA/GO composites are very similar to the spectrum of neat pHEMA showing its characteristic bands C=O (1727 $cm^{-1}$), $CH_2$ (1277 $cm^{-1}$), COC (1158 $cm^{-1}$) and CO or $CH_2$ (1079 $cm^{-1}$). The characteristic bands of GO (D-band at 1350 $cm^{-1}$ and G-band at 1580 $cm^{-1}$) can be found in all Raman spectra of the composites, confirming the presence of GO. Optical microscopy images of pHEMA/GO composites also confirm the presence of GO in the formulations due to the presence of grey/black spots, with pHEMA/GO 5% being completely opaque due to the high amount of filler (FIG. 1).

Figure 5:
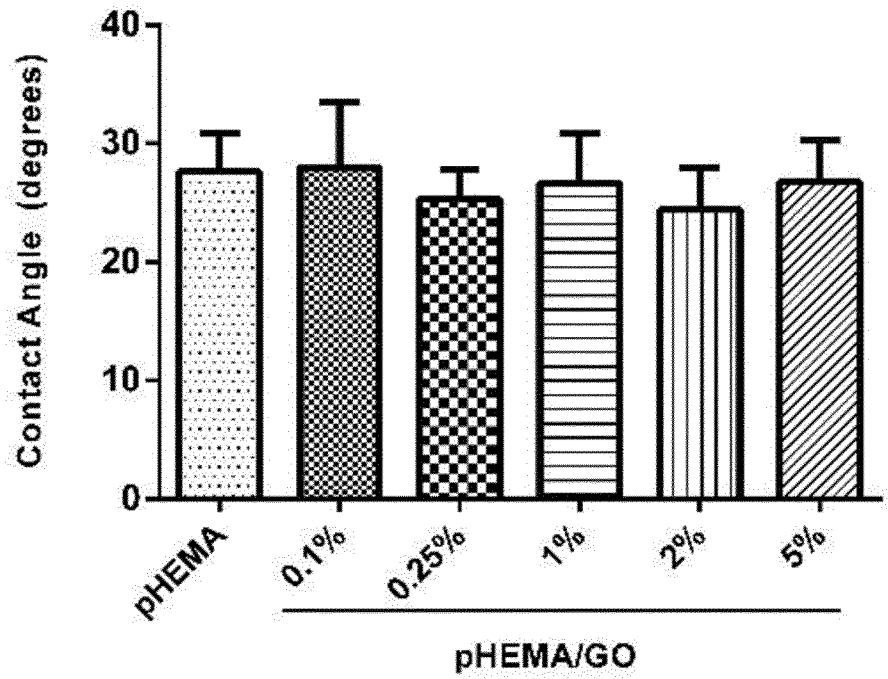
FIG. 5—Captive air-bubble contact angle of hydrated pHEMA and pHEMA/GO composites.

In an embodiment, for 0.1% and 0.25%, GO seems well dispersed, while for 1% and 2% it is possible to identify some aggregates, seen as darker spots. Scanning Electron Microscopy (SEM) imaging of transversal sections of the hydrogel films (FIG. 1) suggests that GO is well distributed and interacts with pHEMA matrix, since it is not possible to identify GO sheets in the fracture surface. GO incorporation increases surface roughness, even at the lowest concentration tested (FIG. 1). GO does not seem to be exposed at the surface of the composite. Despite of these changes in surface topography, no significant differences were observed in the captive air-bubble contact angle of hydrated composites when compared with pHEMA, maintaining a contact angle around 28° (FIG. 5). This shows that the hydrophilic nature of pHEMA surface is not affected by GO incorporation, which is an important feature to keep the non-fouling properties of the material.

Figure 2:
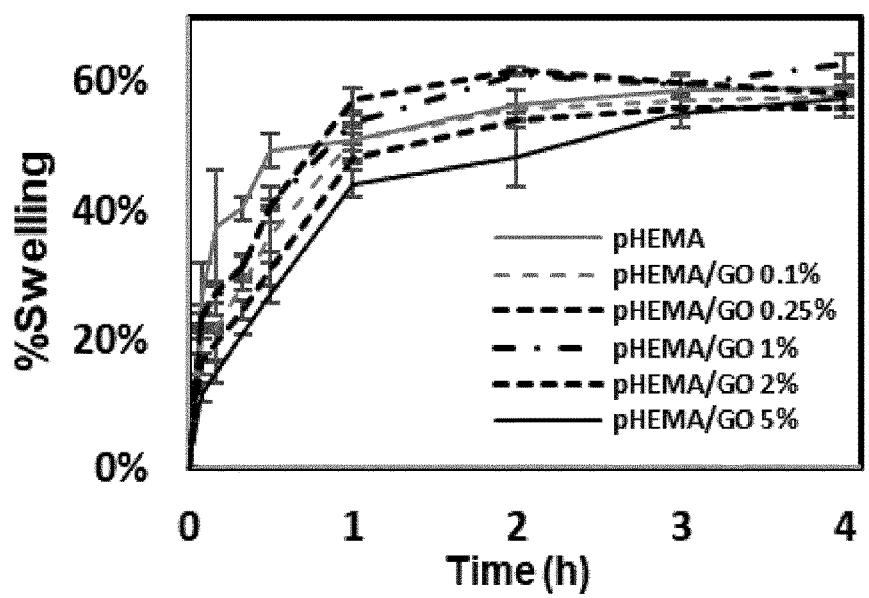
FIG. 2—Swelling degree in water of pHEMA and pHEMA/GO composites.

Water absorption capacity plays a key role in hydrogel applications, since it affects its capacity to adsorb dyes or to deliver drugs and its bio/hemocompatibility. The effect of GO incorporation on the swelling of pHEMA is represented in FIG. 2, showing a slight decrease in the swelling rate for all pHEMA/GO composites between 0 and 0.5 h. This may be due to GO's presence causing pore blockage, or altering the viscoelastic properties of the hydrogel's structure, inducing delayed deformation. However, after 4 h, all materials reach approximately the same swelling value of about 58%, indicating that GO does not affect the equilibrium of water absorption capacity of pHEMA.

Figure 3:
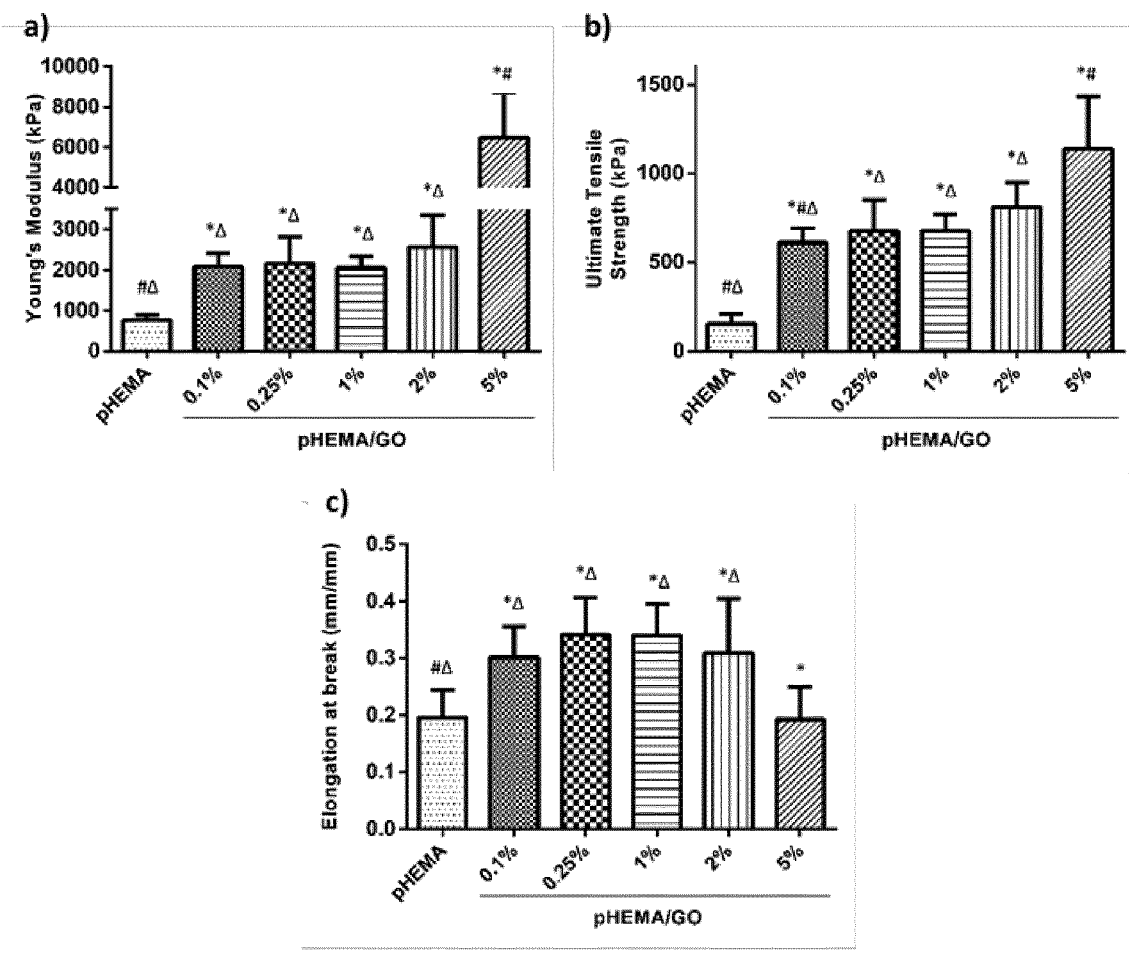
FIG. 3—Effect of increasing GO content on mechanical properties of pHEMA/GO composites: a) Young's modulus, b) Ultimate Tensile Strength and c) Elongation at break. *Different of pHEMA|# Different of pHEMA/GO 2%|ΔDifferent of pHEMA/GO 5%|P<0.05—One Way ANOVA.
Figure 6:
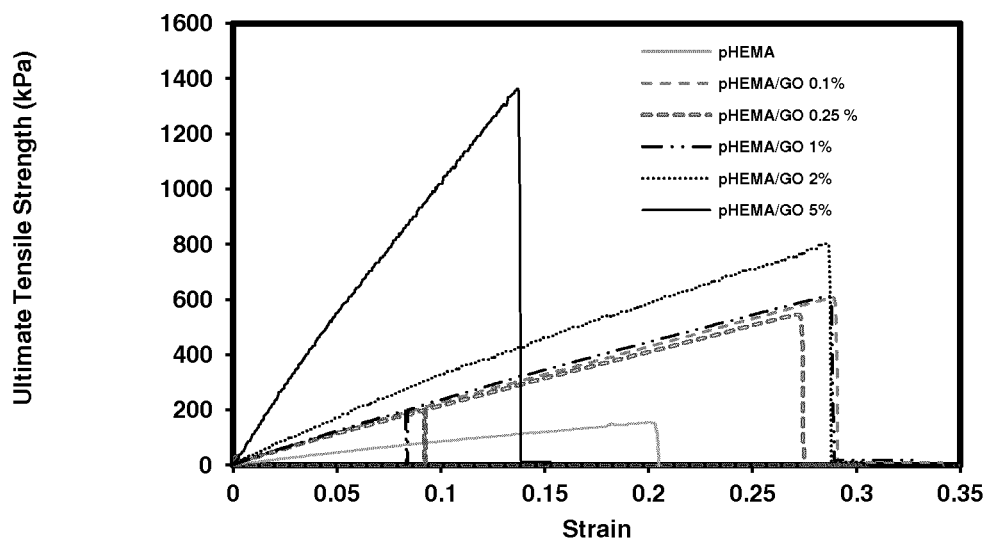
FIG. 6—Representative stress/strain curves of pHEMA and pHEMA/GO composites.

In an embodiment, regarding the mechanical properties, the tensile stress-strain curves obtained for all hydrogels are linear, as shown in FIG. 6 indicating elastic deformation in the entire range of elongation, up to rupture. The stiffness of the composites increases when GO is added, but for loadings between 0.1 and 2% there is no clear trend in Young's modulus (YM) as a function of GO content (FIG. 3a). For 5%, however, the YM is much higher than for the other hydrogels. For pHEMA/GO between 0.1% and 2%, YM is about 3.4 times higher than for neat pHEMA, increasing from $0.76 \times 10^3$ kPa to $2.57 \times 10^3$ kPa. For pHEMA/GO 5% it reaches $6.48 \times 10^3$ kPa (8.5 times higher than pHEMA) reaching stiffness values similar to those of polydimethylsiloxane (PDMS), cartilage or artery walls which are in the order of 1.0 MPa.

In an embodiment, the ultimate tensile strength (UTS) of the composite hydrogels is significantly higher than for neat pHEMA (FIG. 3b). Composites with lower amounts of GO (0.1%-1%) are about 4.4 times stronger than pHEMA, with UTS increasing from 155 kPa to around 680 kPa. For composites with higher amounts of GO this effect is even higher. The UTS of pHEMA/GO 2% and 5% is 5.5 and 7.8 times higher than for pHEMA, respectively. In the pHEMA/GO 5% values reach $1.15 \times 10^3$ kPa, which is remarkable considering that in most hydrogels the UTS is in the order of a few hundred kPa. This level of UTS of pHEMA/GO 2% and 5% is comparable to values of 1 MPa obtained in some polyurethane rigid foams, PDMS and cork. Other studies also report physical incorporation of GO in hydrogel networks, such as on poly(N-isopropyl-acrylamide) (PNIPAM), polyacrylamide (PAM), alginate and hyaluronic acid[2]. However, the increase in UTS in relation to the neat hydrogels was only about 2-3 times, reaching about 400 kPa as reviewed by Alam, A et al.[2] Better compatibility and stronger interaction between oxygenated functional groups of GO and pendant hydroxyl groups in pHEMA network may explain the notable improvement in the mechanical resistance observed in pHEMA/GO composites.

In an embodiment, at lower concentrations (0.1% to 2%), incorporation of GO increases the elongation at break of pHEMA from 0.20 (mm/mm) to about 0.30 (mm/mm) (FIG. 3c). This effect was also observed when physically incorporating GO in epoxy resin and poly(acrylic acid)[2]. The good dispersion of GO and its strong interaction with the polymer network have been pointed as the main reason for the increase in the stretching capacity. However, for pHEMA/GO 5% the elongation at break is similar to pHEMA, indicating that at high concentrations GO agglomeration cancels this effect. Despite of this considerable improvement of pHEMA elasticity, for some applications such as wearable devices an elasticity of around 2 (mm/mm) is necessary[1]. Even higher improvement in the elasticity of pHEMA/GO hydrogels, can be obtained by decreasing the concentration of crosslinking agent (TEGDMA) to half in the formulation of hydrogels. Results show that pHEMA/GO 1% (½ TEGDMA) elasticity is 1.7 times higher than neat pHEMA (Table 1). This effect was previously reported for poly(acrylic acid) hydrogels where decreasing the chemical crosslinker in the presence of GO led to an increase in the stretching capability of the hydrogels without affecting their UTS[2].

TABLE 1

Young's modulus, Ultimate Tensile Strength and Elongation at break of pHEMA, pHEMA/GO 1% and pHEMA/GO 1% with ½ TEGDMA.

|  | Young's modulus (kPa) | Ultimate Tensile Strength (kPa) | Elongation at break (mm/mm) |
| --- | --- | --- | --- |
| pHEMA | 769 ± 333 | 155 ± 40 | 0.20 ± 0.11 |
| pHEMA/GO 1% | $2.05 \times 10^3$ ± 290 | 678 ± 90 | 0.34 ± 0.05 |
| pHEMA/GO 1% (½ TEGDMA) | $1.50 \times 10^3$ ± 270 | 750 ± 150 | 0.50 ± 0.10 |

Figure 7:
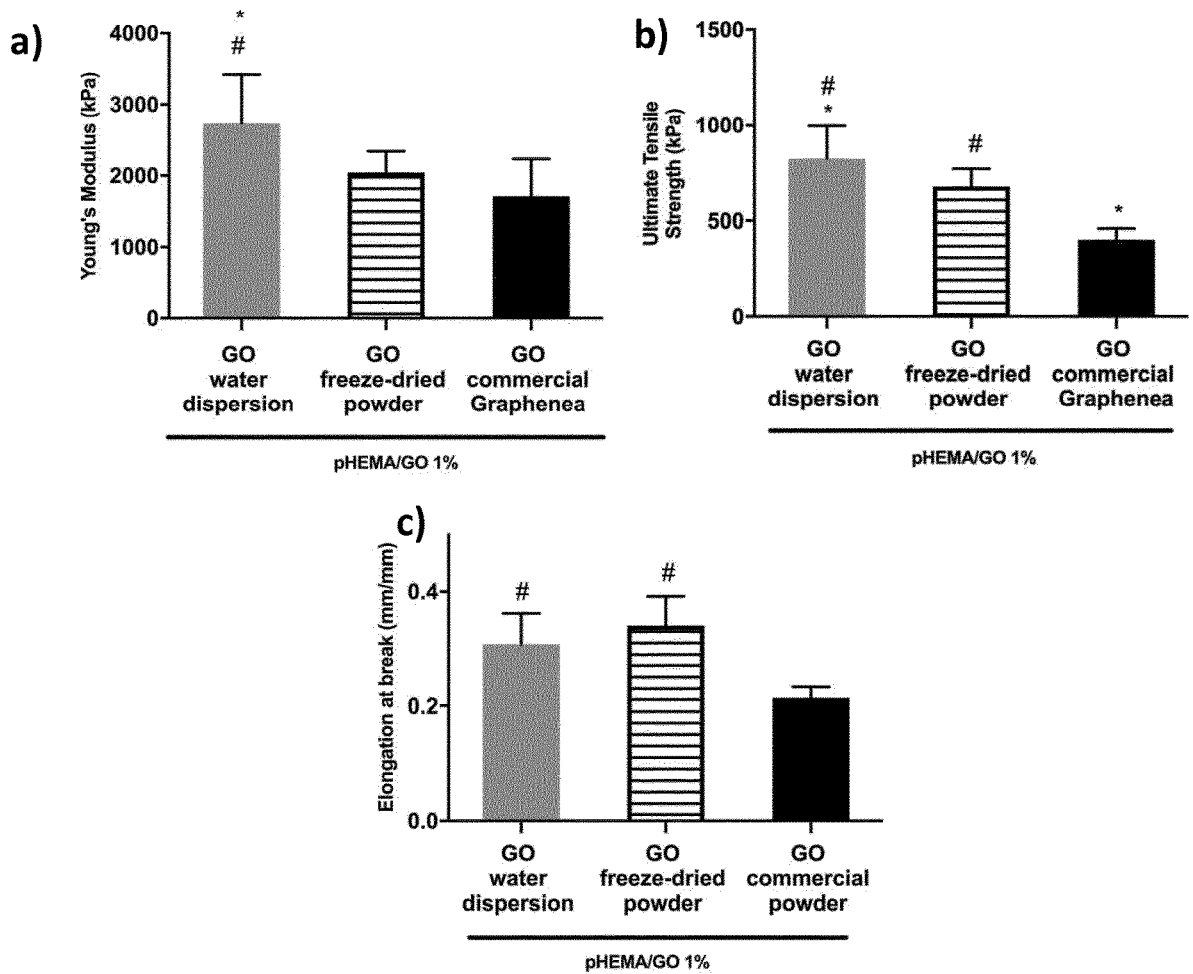
FIG. 7—Mechanical properties of pHEMA/GO 1% composites prepared using different protocols with GO obtained by the method described in the present disclosure in water dispersion/freeze-dried or GO commercial powders: a) Young's Modulus, b) Ultimate Tensile Strength c) Elongation at break. Statistically significantly different from pHEMA/GO 1% using GO freeze-dried powder*, pHEMA/GO 1% using GO commercial powder # ($P<0.05$—One Way ANOVA).

In an embodiment, Graphene oxide (GO) can be incorporated in pHEMA as a dry powder or as an aqueous dispersion. Three different GO's were used: i) GO water dispersion: prepared by oxidation of graphite by modified Hummers' method and 6 h of exfoliation in ultrasonic bath (after these steps GO is dispersed in water from last rinsing); ii) GO freeze-dried powder: GO water dispersion prepared in i) is freeze dried, resulting in a dry powder; and iii) GO commercial powder: GO commercially available (that can be purchased to the company: Graphenea). Different mechanical features were obtained for pHEMA/GO 1% depending on the used GO. FIG. 7 shows that incorporation of GO in water dispersion leads to the highest increase in Young's Modulus (stiffness) and ultimate tensile strength (tensile resistance). However, only a limited amount of GO can be incorporated in the polymer network, with the highest loading of GO being 1% (w/v) (131 mg is the maximum mass of GO that can be incorporated in the water content of the pHEMA formulation (1.5 ml in 13.1 mL total volume)). Freeze drying the GO dispersion allowed obtaining GO powders that can be incorporated in higher amounts in pHEMA up to 5% (w/v). Results also show that incorporation of freeze-dried GO powder in pHEMA leads to higher resistance to tensile stress than using of commercially available GO powder.

Figure 19:
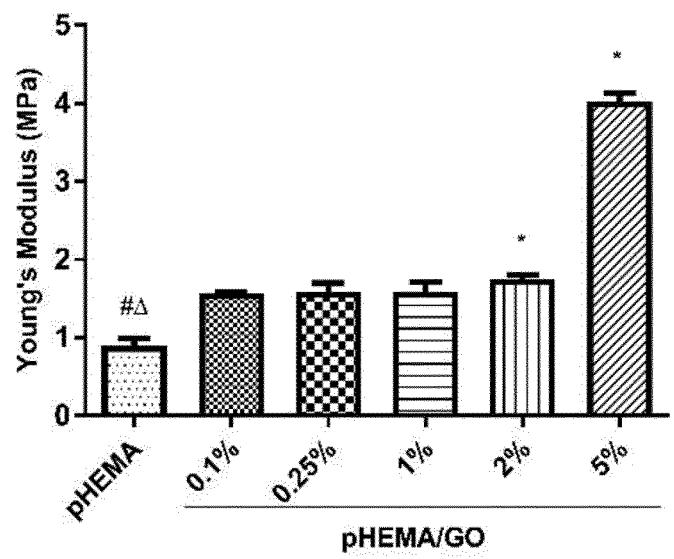
FIG. 19—Young's modulus of pHEMA and pHEMA/GO composites under compression stress. Statistically different of pHEMA (*), different of pHEMA/GO 2% (#) and different of pHEMA/GO 5% (Δ) ($P<0.05$—Kruskal-Wallis test).

In an embodiment, the YM of pHEMA/GO hydrogels was also evaluated under compressive stress. The results show an increase of 4 times of pHEMA YM with incorporation of 5% GO reaching 3.79 MPa (FIG. 19). This stiffness enables the application of pHEMA/GO hydrogels in designing of replacement biomaterials for cartilage (YM=0.6 MPa) and/or intervertebral disc (0.4-3 MPa).

Figure 4:
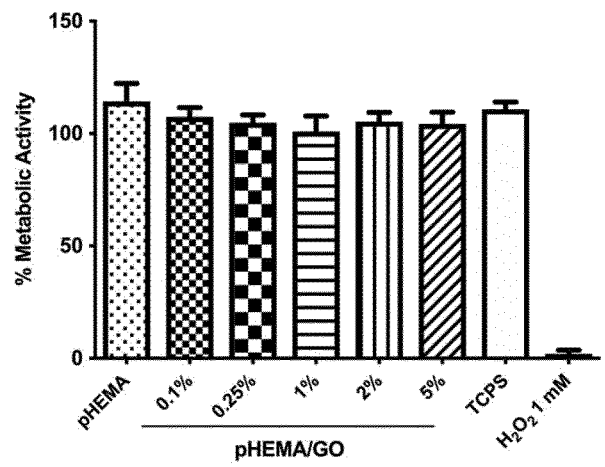
FIG. 4—Metabolic activity of NIH 3T3 cells after incubation with medium extracts (using DMEM as extraction vehicle) during 24 h. The metabolic activity of cells is represented in percentage in comparison of cells growing in DMEM+ (100%). Extracts of TCPS discs were used as positive control while a solution of 1 mM $H_2O_2$ (in DEMEM+) was used as negative control. According to ISO 10993-5:2009(E), 70% of metabolic activity is the lower limit to consider the material extracts cytotoxic (red line).

Biocompatibility of the pHEMA/GO hydrogels was evaluated by measuring possible cytotoxic effects of medium extracts using a cell line of mouse fibroblasts (NIH 3T3 cells). The results show that none of the obtained extracts from the materials affects the metabolic activity of the cells (FIG. 4), confirming lack of cytotoxicity and opening a wide range of possibilities for biomedical applications.

Nowadays, pHEMA has been used for production of contact lenses, keratoprosthesis, drug delivery systems, wearable devices to stimulate wound healing, soft tissues, and as coating for implantable devices (such as orthopedic, catheters, etc). Taking into account the great improvement in stiffness and tensile resistance, without affecting its intrinsic characteristics, the new pHEMA/GO hydrogels reported here will pave the way for new applications of pHEMA. Regarding the biomedical field, pHEMA/GO hydrogels could be potentially applied in engineering of load bearing tissues, such as cartilage, intervertebral disc, blood vessels, cardiac valves, design of innovative implantable devices such as catheters, vascular grafts and hernia repair devices. Uses in other areas can be envisaged, like in soft robotics, packaging, sealing, and sensors.

In an embodiment for the designing of strong pHEMA/GO based hydrogels, a good strategy to promote an even higher reinforcement is GO functionalization aiming to improve its interaction with pHEMA network. For PNIPAM and PAM hydrogels, the incorporation of functionalized GO leads to enhanced resistance to compression and increased stiffness, respectively, when comparing with incorporation of neat GO. Moreover, the pHEMA/GO hydrogels of the present disclosure were easily produced by casting, meaning that we can modulate the 3D architecture of pHEMA/GO hydrogels to potentiate their resistance to tensile and compressive stress.

Another aspect of the present disclosure relates to a method for producing biocompatible hydrogels with outstanding stiffness and tensile resistance, through in situ incorporation of GO during pHEMA polymerization. The mechanical properties can be tuned varying the amount of GO and crosslinking agent. The water absorption capacity, surface wettability and biocompatibility of pHEMA are not compromised by GO addition.

Figure 8:
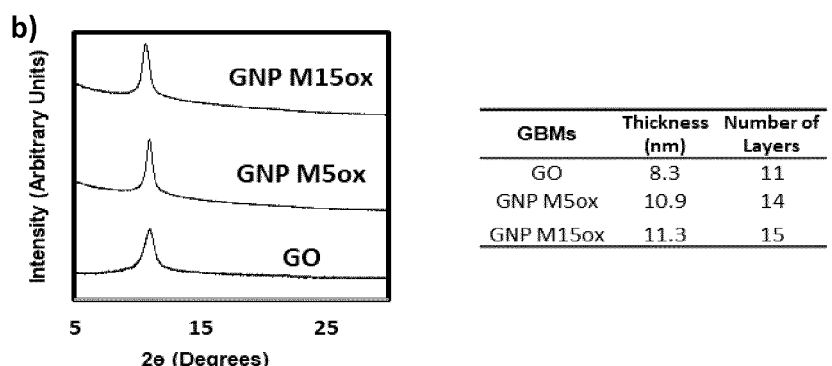
FIG. 8—Characterization of GM regarding oxidation degree, morphology, thickness and number of layers: a) XPS analysis of atomic concentrations and chemical groups and b) XRD analysis of GM powders and oxidized-GM powders in the case of XRD analysis.

In an embodiment, the effect of different GM in the mechanical reinforcement of pHEMA was evaluated. For this, graphene oxide (GO) and two commercially available non-oxidized GM, GNP M5 and GNP M15 (which have different lateral sizes, 5 µm and 15 µm, respectively), as well as their oxidized forms, GNP M5ox and GNP M15ox were explored. Chemical composition of GM powders was evaluated by XPS (FIG. 8a). Non-oxidized GM, namely GNP M5 and GNP M15, present low oxygen content in their composition (about 4%). In the oxidized forms of the tested GM, GO, GNP M5ox and GNP M15ox, the atomic percentage of oxygen was about 34%, confirming the successful oxidation of the materials. In the oxidized materials the most prevalent groups were hydroxyl, epoxy and ketones while carboxyl groups were in much lower amounts (FIG. 8a).

SEM imaging of GM powders revealed that non-oxidized GM particles are planar with sharp edges while oxidized GM particles exhibit a wrinkled structure with folded edges (FIG. 8b). TEM images show that GO has lateral size of about 1.5 µm while GNP M5/M15 and their oxidized forms have a lateral size of around 5 and 15 µm, respectively. Moreover, GO is the GM with a higher exfoliation degree. The exfoliation degree of oxidized GM was evaluated by XRD. FIG. 8c shows that $2\theta$ of oxidized-GM is about 10.2° for GO and 10.6° for GNP M5ox and GNP M15ox meaning that exfoliation degree of these materials is higher than graphite ($2\theta$=26.1). XRD peak of GO is broader than GNP M5ox which is indicative of a higher exfoliation. Through the Scherrer and Bragg's equation is possible to determine the thickness and no layers (FIG. 8c). The results of the used GM on the present disclosure showed that the thickness of GO is 8.3 nm (corresponding to 11 layers) while GNP M5ox and GNP M15ox is 10.9 and 11.3 (corresponding to 14-15 layers), respectively. Taking into account the supplier information, the thickness of non-oxidized GM is lower than oxidized GM. This could be associated to the increase of the d-spacing due to the intercalation of oxygen containing functional groups in between the oxidized GM layers.

Fourier-transform infrared spectroscopy (FTIR) spectra of neat pHEMA and composites show the characteristic stretching bands of the polymer, namely C=O (1727 $cm^{-1}$), $CH_2$ (1277 $cm^{-1}$), COC (1158 $cm^{-1}$) and CO or $CH_2$ (1079 $cm^{-1}$). Moreover, the inexistence of the bands of C=C bonds at 815 $cm^{-1}$, 943 $cm^{-1}$ and 1620-1680 $cm^{-1}$, which are associated to HEMA monomers, indicates full polymerization of the pHEMA in the presence of all GM.

Figure 10:
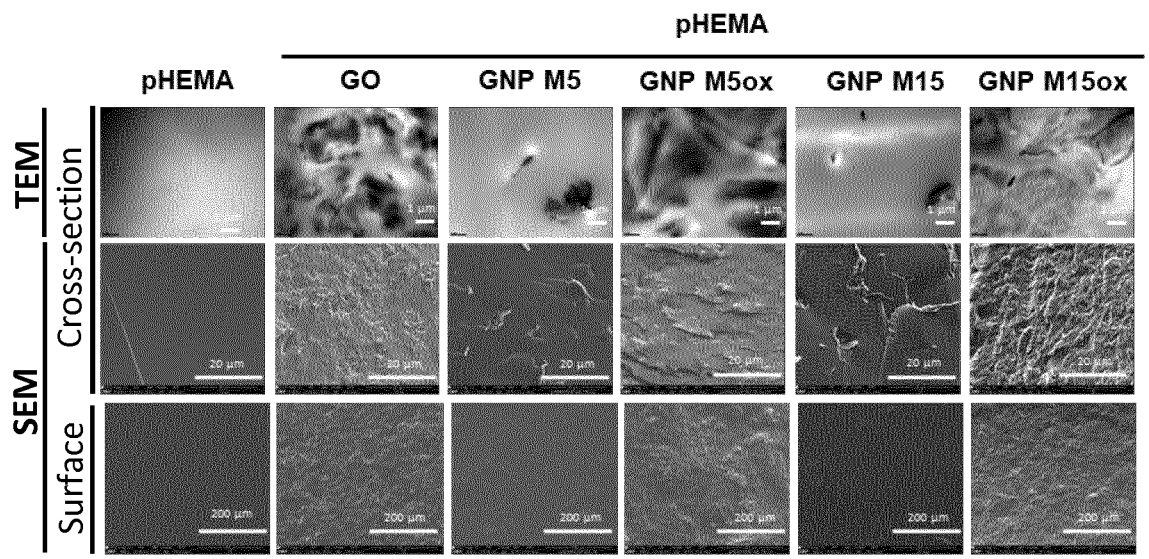
FIG. 10—TEM (first line) and SEM (lines 2 and 3) images of pHEMA and pHEMA/GM composites ultrathin section, fracture and surface, respectively.

GM dispersion in pHEMA was assessed by TEM imaging of ultrathin sections and SEM cross-sections of polymer composites (FIG. 10). Results show that oxidized GM are well dispersed in the polymer matrix while non-oxidized GM tend to be less dispersed in the polymer network as suggested. Regarding the cross-section fracture of pHEMA/GNP M5 and pHEMA/GNP M15 composites, it was possible to identify some individualized GNP M5 or GNP M15 sheets. This effect suggests a weaker interaction between non-oxidized forms of GM with polymeric network of pHEMA comparing with oxidized GM. FIG. 10 also shows that the cross-section of pHEMA is smooth but after incorporation of GM there is an increase in the roughness of the fracture surface, which is potentiated in oxidized forms of GM (GO, GNP M5ox or GNP M15ox). Moreover, it is not possible to identify GO, GNP M5ox or GNP M15ox platelets in the surface fracture, which suggests that particles are distributed and interact well with polymeric network of pHEMA.

Surface topography of pHEMA/GM composites was evaluated by SEM, revealing that incorporation of GM increased surface roughness of pHEMA (FIG. 10). This effect is emphasized when oxidized forms of GM are incorporated. In the case of pHEMA/GNP M5 and pHEMA/GNP M15 composites, some platelets seem to be exposed at the surface while in pHEMA/GO, pHEMA/GNPox M5 and pHEMA/GNPox M15 composites, GM seem to be completely covered by the polymer.

Figure 11:
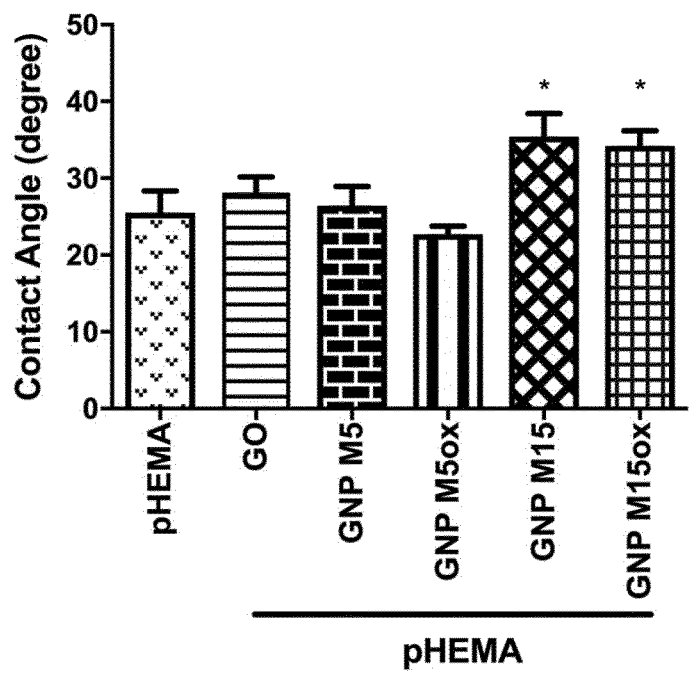
FIG. 11—Captive air-bubble contact angles of hydrated pHEMA and pHEMA/GM composites.

Surface wettability of pHEMA/GM composites was assessed by evaluation of the captive air-bubble contact angle. FIG. 11) shows that the incorporation of GNPs with smaller lateral size, namely GO and both forms of GNP M5, did not induce a significant alteration in surface wettability of pHEMA, which is approximately 25°. Larger GNPs (GNP M15 and GNP M15ox) decrease surface hydrophilicity in around 10°, presenting a contact angle of approximately 35°.

Figure 12:
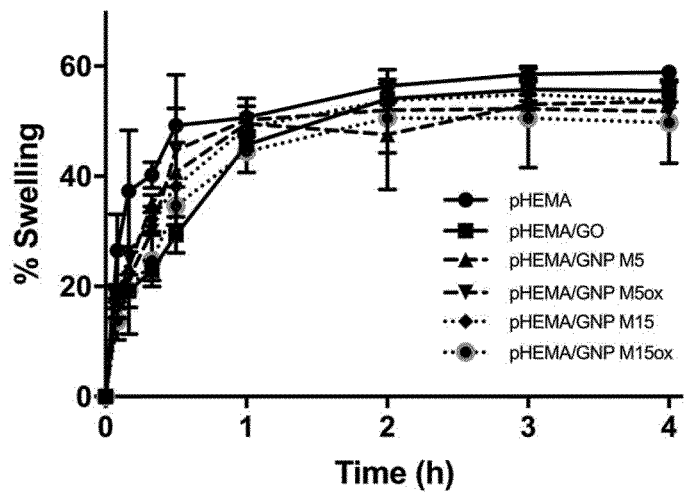
FIG. 12—Swelling capacity of pHEMA and pHEMA/GM composites.

In an embodiment, swelling profile of pHEMA/GM composites was assessed through gravimetric analysis of dehydrated films in water for 4 hours (FIG. 12). None of the incorporated GM affected significantly the swelling profile and total water absorption capacity of pHEMA, which is around 55%.

Figure 9:
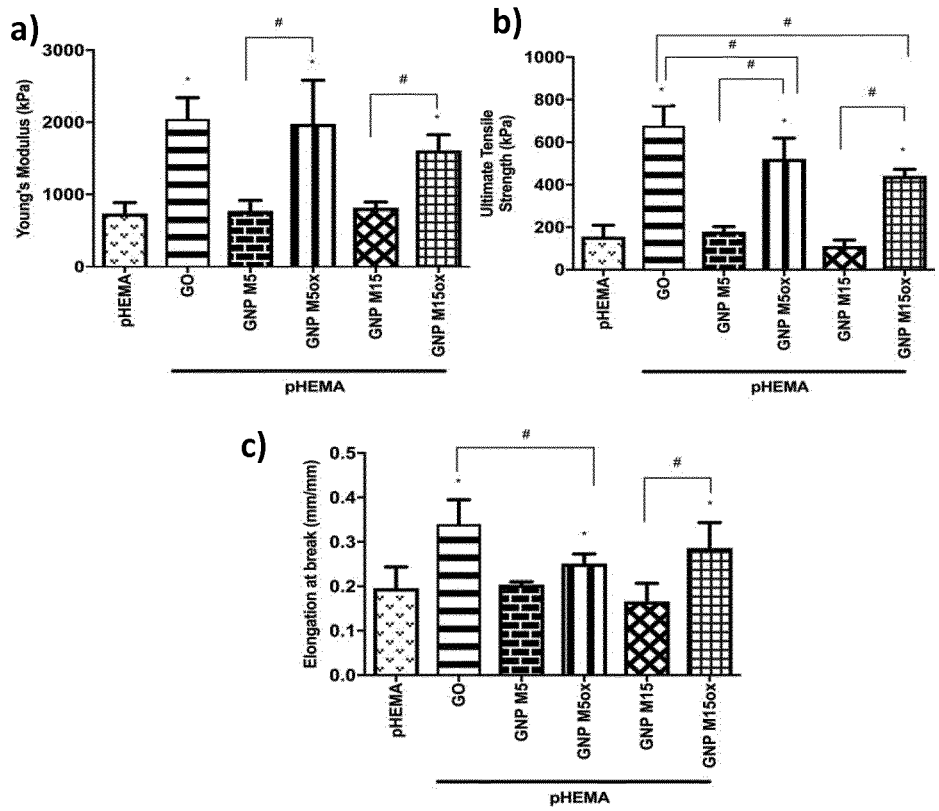
FIG. 9—Mechanical properties of pHEMA and pHEMA/GM composites: a) Young's Modulus, b) Ultimate Tensile Strength, c) Elongation at break. Statistically significantly different from pHEMA (*) and different between each sample (#) ($P<0.05$; One Way ANOVA).
Figure 18:
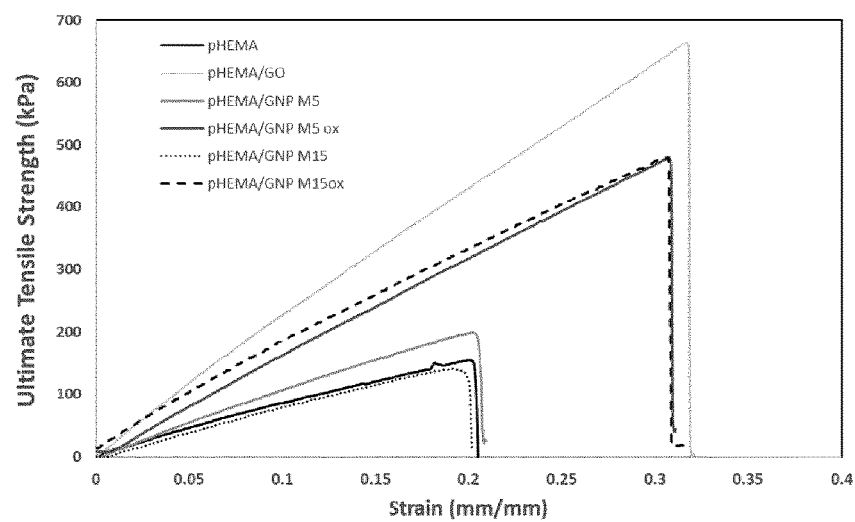
FIG. 18—Representative stress/strain curves of pHEMA and pHEMA/GO composites.

Regarding the mechanical properties of pHEMA/GM composites, all the materials have a linear stress-strain curve, characteristic of an elastic behavior of materials until rupture (FIG. 18). Incorporation of oxidized forms of GM increased Young's Modulus of pHEMA 2.5 times (from 744 kPa to $1.8 \times 10^3$ kPa) while non-oxidized forms did not have any effect in pHEMA stiffness (FIG. 9a). Since similar results were obtained for GNP M5 and GNP M15, as well as for GNP M5ox and GNP M15ox, this effect is independent of particles lateral size.

As observed for stiffness, the presence of non-oxidized GNPs did not influence the tensile resistance of pHEMA, maintaining the ultimate tensile strength values of around 150 kPa (FIG. 9b). GMBs oxidization increased the tensile resistance in 4.4×, 3.4× and 2.8× when GO, GNP M5ox and GNP M15ox were used as fillers, respectively, reaching values as high as 678 kPa for GO.

Figure 13:
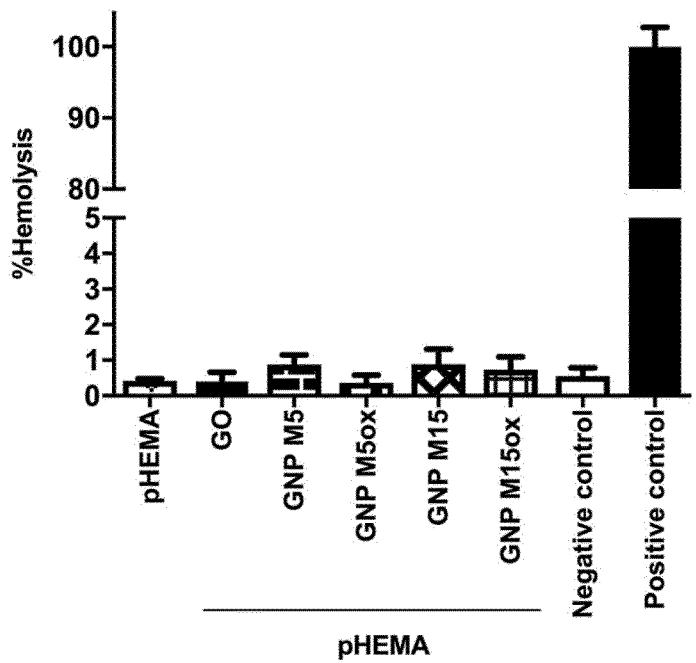
FIG. 13—Hemolytic potential of pHEMA and pHEMA/GM composites. PBS and 1% Triton were used as negative and positive control of red blood cells lysis, respectively.

Elongation at break is the measurement of polymers elasticity. Results showed that pHEMA and composites with GNP M5 and GNP M15 have an elongation at break of approximately 0.2 mm/mm (FIG. 9c). The incorporation of oxidized-GM led to an increase of elasticity of pHEMA, reaching values around 0.27 mm/mm for GNP M5ox and GNP M15ox, and 0.34 mm/mm for GO, almost doubling its elasticity in this last filler. In an embodiment, FIG. 13 shows the hemolytic potential of pHEMA and pHEMA/GM composites. Hemolytic ratio of all tested materials were lower than 1% which is in the permissible limit set by ISO 10993-4 standard for hemocompatible materials 5%).

Figure 14:
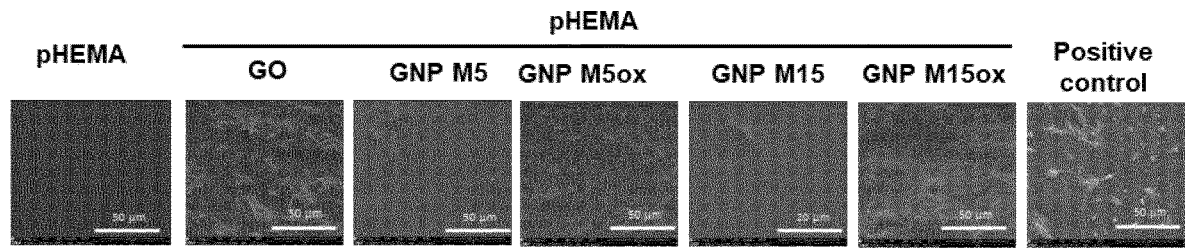
FIG. 14—SEM images of pHEMA and pHEMA/GM composites surface after 1 h incubation with human platelets at 37° C.

In an embodiment, platelet adhesion and activation to pHEMA/GM composites surface were evaluated through the incubation of materials with human platelets concentrate (PC) (FIG. 14). pHEMA revealed to be a non-fouling material, with no platelets adhered. Furthermore, none of the incorporated GM affected platelets adhesion and activation in pHEMA, even in the presence of plasma proteins that could promote platelet adhesion and activation to the surface.

Figure 15:
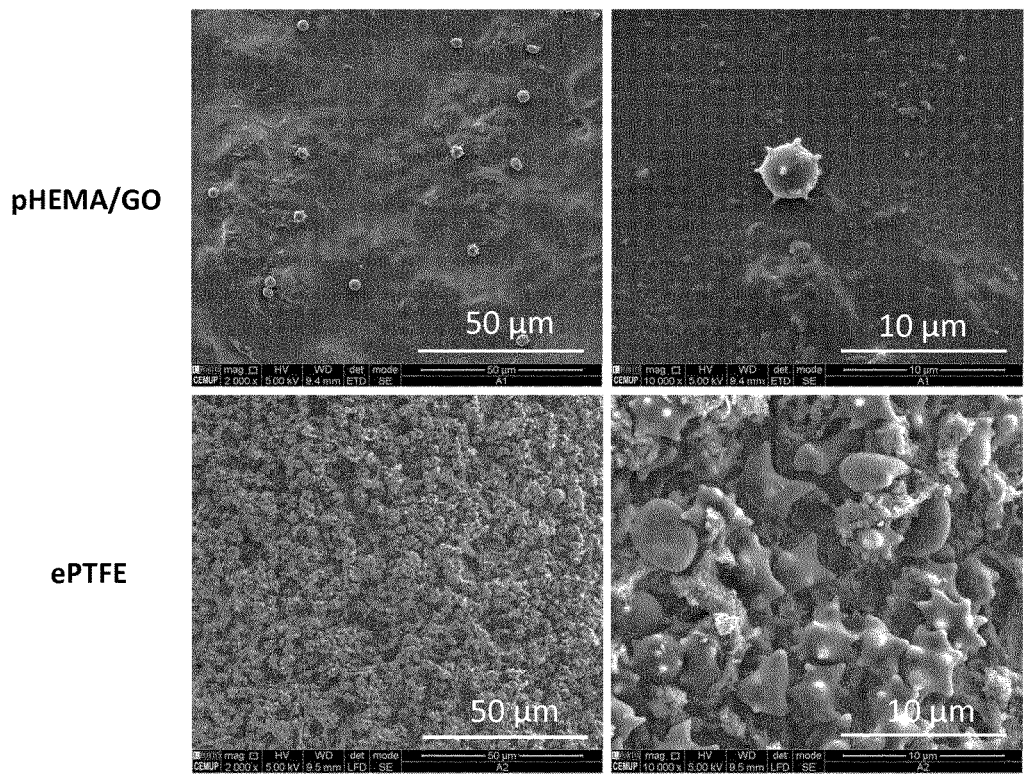
FIG. 15—SEM images of the lumen of pHEMA/GO 1% and ePTFE conduits upon 1 h in contact with circulating blood by AV-shunt in pigs.

SEM images of pHEMA/GO lumen upon 1 h in contact with circulating blood show a few adhesion of leucocytes at its surface (FIG. 15). Oppositely, ePTFE, which is currently used in clinics for large diameter vascular grafts, reveals exuberant platelet, red blood cells, leucocytes adhesion showing a clot formation with high content of fibrin fibers.

Figure 16:
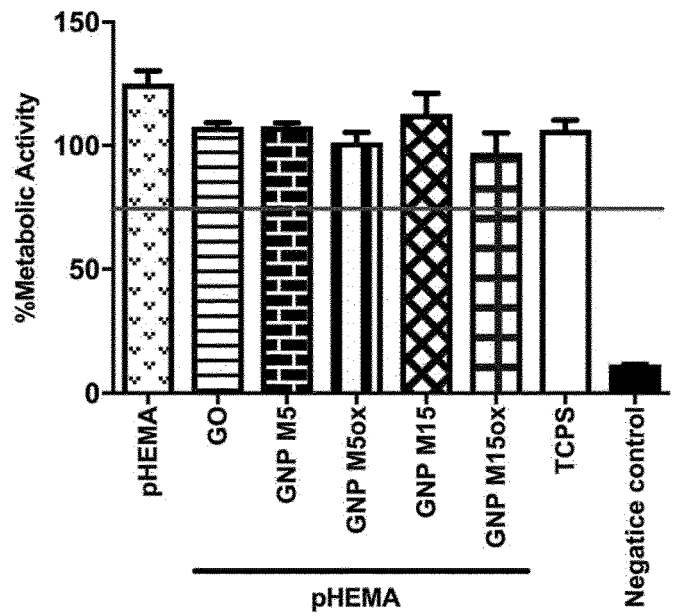
FIG. 16—Metabolic activity of HUVECs cells after 24 h incubation with extracts of pHEMA and pHEMA/GM (M199+ as extraction vehicle). The metabolic activity of cells is represented in percentage in comparison to cells growing in M199+(100%). Extracts of TCPS discs were used as positive control and 1 mM $H_2O_2$ (in M199+) was used as negative control. According to ISO 10993-5:2009 (E), 70% of metabolic activity is the lower limit to consider the material extracts cytotoxic (red line).

In an embodiment, the biocompatibility of pHEMA/GM hydrogels was evaluated by measuring possible cytotoxicity of medium extracts using cell line of endothelial cells (Human Umbilical Vein Endothelial Cells-HUVECs). The results showed that none of the obtained extracts from the materials affects the metabolic activity of the cells (FIG. 16) confirming lack of cytotoxicity.

Figure 17:
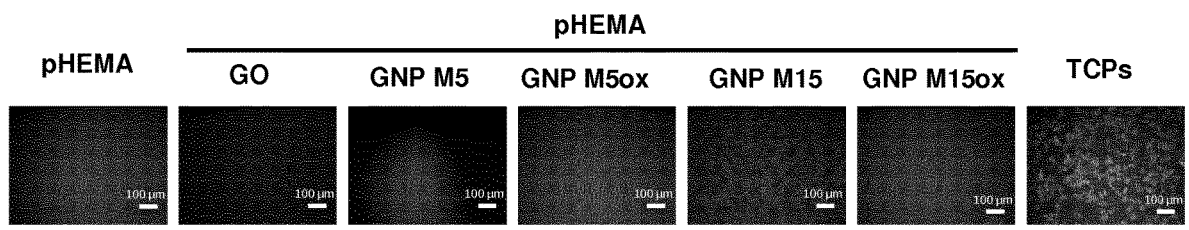
FIG. 17—HUVECs adhesion and proliferation on pHEMA and pHEMA/GM composites after 48 h seeding at materials surface. TCPS discs were used as positive control of cell adhesion. On the top, fluorescence microscopy images of adherent cells stained with DAPI (blue) and phalloidin (green).

In an embodiment, FIG. 17 displays HUVECS adhesion after 48 h incubation on pHEMA/GM composites surface. Fluorescence microscopy images show the low or inexistent adhesion of cells on the surfaces, which was confirmed by the very low cell metabolic activity (lower than 10%) comparing to the control without materials. As such, the incorporation of GM in pHEMA did not promote the adhesion or proliferation of cells on the surface of pHEMA or pHEMA/GM composites, confirming the non-fouling properties of these materials.

In an embodiment, was evaluated the effect of oxidation, thickness and lateral size of GM in the mechanical reinforcement of pHEMA regarding the development of new materials to produce blood contacting medical devices. For this, 5 different GM types were tested: a) non oxidized GM, namely multilayer micro graphene GNP M5 and GNP M15, which differ only in platelet diameter (~5 µm for GNP M5 and ~15 µm inn for GNP M15) and b) oxidized GM, namely single layer GO, and multilayer GNP M5ox and GNP M15ox, which were obtained from oxidation of graphite, GNP M5 and GNP M15, respectively.

In an embodiment, the low percentage of oxygen 4%) in the chemical composition determined by XPS for non-oxidized GM can been associated to GNPs preparation process that consists in graphite intercalation and thermal exfoliation leading to the addition of oxygen groups in GNP edges in C/O ratio of 24/1, as described in the specification sheet of the supplier. XPS analysis also confirmed the successful oxidation of GNPs and Graphite by modified Hummers' method, resulting in a C/O ratio of 2:1 for all oxidized GM materials. The most prevalent groups found in the oxidized GM were epoxides, hydroxyl and ketones while the carboxylic groups that have been described in the edges of platelets are less abundant. The oxidative state of GM is closely associated to their morphology, being the oxidized GM sheets randomly stacked, wrinkled and with folded edges while non-oxidized platelets are flatter with sharper edges. This effect is due to the presence of epoxide, hydroxyl and a few carboxyl groups in oxidized forms of GM which leads to the formation of hydrogen bonds within each layer (wrinkled or folded edges) or inter layers (random stacking). XRD results are in accordance, revealing that oxidized GM have a higher interlayer distance than non-oxidized forms. This effect is associated to the presence of oxygen groups in graphene layers which promotes a higher dispersion of the GM layers.

In an embodiment, the incorporation of GO with monomers before in situ polymerization has been reported to allow a better dispersion and good interaction between GM and polymeric networks. However, the better dispersion of oxidized GM in pHEMA network comparing to non-oxidized forms can be related to the presence of oxygen groups in the oxidized GM, which establish a stronger interaction with side chains of pHEMA. Still, the incorporation of GM did not affect the polymerization of pHEMA, since FTIR spectra of pHEMA and pHEMA/GM were very similar and none of them present the characteristic bands of C=C bonds which are associated to HEMA monomers.

In an embodiment, the incorporation of either type of oxidized-GM induced a great alteration of surface morphology, with an increase of surface roughness, despite only the larger GNPs (GNP M15 and GNP M15ox) inducing small alteration in surface wettability (becoming less hydrophilic). Despite the water contact angle of GO being 67.4° and graphene being 90°-100°, SEM images of pHEMA/GM composites show that GM are not exposed at the surface which could explain the low or non-alteration of pHEMA wettability. However, it is important to highlight that previous studies reported that GM incorporation on other polymers, such as polyacrylamide, polylactic acid, polyvinyl chloride, poly(vinylidene fluoride) leads to significant changes in surface wettability of neat polymers. Nevertheless, the hydrophilic nature and swelling capacity of the hydrogels are conserved upon GM incorporation, important characteristics to maintain the non-fouling properties (low protein and cell adhesion).

GM have been described with outstanding mechanical properties, which make these materials great candidates for the reinforcement of polymers. Single layer graphene has a stiffness of 1 TPa and ultimate tensile strength of 130 GPa$^3$. The stability of $sp^2$ bonds that form the honey-comb structure of graphene has been pointed as the main reason of this impressive resistance. However, defects, wrinkling, crumpling and stacking of graphene sheets affects considerably the mechanical resistance of graphene. Taking into account the features of GO (more defects in sheets and $sp^a$ bonds) it is expected that its mechanical properties are not as remarkable as single layer graphene. Indeed, the stiffness of graphene oxide paper, obtained from deposition of single layer graphene oxide, is 40 GPa and the ultimate tensile strength is 120 MPa$^3$. Despite being conceptual that non-oxidized GM have a higher mechanical resistance than the oxidized GM, we observed that only the oxidized GM were efficient in the mechanical reinforcement of pHEMA. This fact could be associated to a stronger interaction between the epoxide, hydroxyl and carboxyl groups of oxidized GM with the lateral chains of pHEMA that contain hydroxyl and ester groups. This stronger interaction of oxidized GM with polymers network has also been reported for polyacrylamide and polyvinyl alcohol as reviewed by Papageorgiou et al$^3$.

Besides the oxidation degree of GM, the lateral size of GM flakes is also described to play a critical role in the mechanical reinforcement of polymers$^3$. It has been suggested that GM flakes with lateral size higher than 8 μm induces a better reinforcement of composites$^3$. However, we herein found no significant differences in the tested mechanical features between GNP with 5 and 15 μm (neither between GNP M5 and pHEMA/GNP M15 nor between pHEMA/GNP M5ox and pHEMA/GNP M15ox).

In an embodiment, pHEMA/GO 1% (w/v) composites of the present disclosure showed the highest resistance to tensile stress. This fact could be explained by better dispersion of GO in pHEMA since efficiency of oxidized-GM in polymers reinforcement seems to be independent of their exfoliation degree$^3$.

In an embodiment, non-fouling features and biocompatibility of pHEMA are important to allow its application in the design of contact lens and keratoprosthesis. GM incorporation did not affect human platelets adhesion/activation nor HUVECs adhesion/proliferation on hydrogel's surface. The preservation of pHEMA surface hydrophilicity upon GM incorporation could explain this maintenance of non-fouling behaviours, given the correlation between surface features and interaction of proteins, platelets and cells.

In spite of the results of the hydrogel of the present disclosure specifies a non-effect in surface features of pHEMA upon GM incorporation previous studies showed that GNP incorporation in PLA increased its surface hydrophobicity and reduced platelet activation in the presence of plasma proteins while incorporation of GO in polyetherimide increased its hydrophilicity and prevents platelets adhesion. There are two studies that report a higher adhesion and proliferation of HUVECs in surface of composites containing GM, namely GO/polyurethane and reduced graphene oxide (rGO)/poly(vinylidene fluoride). In these cases, there was no reference to GM exposition at polymer surface nor to surface wettability and the base polymers did not exhibit non-fouling properties. Altogether, the effect of GM in adsorption of proteins and adhesion of platelets and cells is dependent of based polymer features, GM type and exposure and also surface features of resultant composite.

Regarding cytotoxicity of the developed composite hydrogels, the non-hemolytic potential verified for all the materials is in agreement with previous studies which showed non-hemolytic potential of GM when incorporated in composites. Cytotoxicity studies showed that composites extracts are not cytotoxic for HUVECs.

Taking into account the mechanical features and bio/hemocompatible properties of the herein developed pHEMA/GM composites, these new materials have a high potential to be applied in the design of many well-known blood contacting biomaterials (table 2). A human aortic valve has ultimate tensile strength (circumferential) of 750-2500 kPa and elongation at break of 0.10-0.17 mm/mm. The mechanical properties obtained for pHEMA/GO composites (Young's modulus ≅2100 kPa, ultimate tensile strength ≅680 kPa and elongation at break ≅0.30 mm/mm) are very similar to these, to currently used porcine aortic valves (Ultimate Tensile Strength (circumferential) ≅1000 kPa and elongation at break ≅0.23 mm/mm) and to other materials under research like tissue engineered fabricated porous polyhydroxyalkanoate heart valves (Young's modulus ≅3000 kPa, Ultimate Tensile Strength (circumferential) ≅700 kPa and elongation at break ≅0.33 mm/mm). The design of vascular grafts could be another future application for these pHEMA/GM hydrogels. Tensile resistance of native veins and arteries is about 1000 kPa while elongation at break rounds the 0.50 mm/mm for saphenous vein. However, blood vessels display a J-shaped stress-strain response, which should be something to take into consideration in further optimizations of pHEMA/GM composites for this application. Catheters are another potential application of pHEMA/GM hydrogels. The Young's modulus of silicon catheters is 1000-2000 kPa, very similar to the obtained for the composites of the present disclosure, despite silicon catheters having higher resistance to tensile stress (2000-3000 kPa) and elasticity (4 mm/mm). Nevertheless, the lower elasticity of the composites of the present disclosure may not be an issue for this application, since catheters made from other polymers such as polyurethane have elasticity in the elastic part of tensile resistance similar to obtained values for pHEMA/GO.

TABLE 2

Comparison between mechanical features of pHEMA/GO 1% and blood contacting devices

| Material | Young's Modulus (kPa) | Ultimate Tensile Strength (kPa) | Elongation at Break (mm/mm) |
| --- | --- | --- | --- |
| Hydrogel of the present disclosure (pHEMA/GO 1% (w/v)) | 2100 | 689 | 0.30 |
| Porcine aortic valve | — | 1000 | 0.23 |
| Human aortic valve | — | [750-2500] | [0.10-0.17] |
| Tissue engineered heart valves | 3000 | 700 | 0.33 |
| Native saphenous vein | — | 1000 | 0.50 |
| Internal thoracic artery | — | 1000 | 1.5 |
| Silicon Catheter | 1000-2000 | 2000-3000 | 4.0 |

Five different types of GM, varying regarding oxidation degree, thickness and lateral size, were successfully incorporated in pHEMA. In spite of the increase on surface roughness of pHEMA, more predominant when the oxidized GM were incorporated, wettability and swelling capacity of pHEMA were not significantly affected independently of the GM incorporated, except for larger nanoplatelets (GNP M15 and GNP M15ox). Regarding the mechanical reinforcement of pHEMA, oxidation degree and lower thickness of GM (as well particles dispersion) revealed to be crucial factors to achieve the greater improvements in the mechanical properties of pHEMA, while particles lateral size had a minor effect. As such, GO was the most efficient filler among the tested GM in the increase of stiffness and tensile resistance. All the pHEMA/GM composites exhibited negligible levels of blood platelets adhesion and activation, non-hemolytic potential and non-cytotoxicity. Thus, materials developed in this study are promising to apply in the designing of new blood contacting devices.

The term "comprising" whenever used in this document is intended to indicate the presence of stated features, integers, steps, components, but not to preclude the presence or addition of one or more other features, integers, steps, components or groups thereof.

Where singular forms of elements or features are used in the specification of the claims, the plural form is also included, and vice versa, if not specifically excluded. For example, the term "a hydrogel" or "the hydrogel" also includes the plural forms "hydrogels" or "the hydrogels," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

The following reference are herewith entirely incorporated:

1 Y. S. Zhang, A. Khademhosseini, Advances in engineering hydrogels, Science 356(6337) (2017).

2 Alam A, Zhang Y, Kuan H-C, Lee S-H, Ma J. Polymer composite hydrogels containing carbon nanomaterials—Morphology and mechanical and functional performance. Progress in Polymer Science (2017).

3 A. M. Pinto, C. Gonçalves, D. M. Sousa, A. R. Ferreira, J. A. Moreira, I. C. Gonçalves, F. D. Magalhães, Smaller particle size and higher oxidation improves biocompatibility of graphene-based materials, Carbon 99(Supplement C) (2016) 318-329.

4 Papageorgiou D G, Kinloch I A, Young R J. Mechanical properties of graphene and graphene-based nanocomposites. Progress in Materials Science 90, 75-127 (2017).

5 Goncalves I C, Martins M C, Barbosa M A, Ratner B D. Protein adsorption and clotting time of pHEMA hydrogels modified with C18 ligands to adsorb albumin selectively and reversibly. Biomaterials 30, 5541-5551 (2009).

The invention claimed is:

1. A medical device comprising a non-fouling hydrogel comprising poly(2-hydroxyethyl methacrylate) and at least 1%-2% w/v of graphene material,
    wherein the oxidation degree of the graphene material is between 30-50% oxygen atomic percentage,
    wherein the graphene material is incorporated in the hydrogel,
    wherein the graphene material comprises multi-layer graphene oxide having 3-12 layers, and
    wherein the lateral size of graphene material varies between 1-4 µm; and 2-10% w/w of a crosslinking agent.

2. The medical device according to claim 1, wherein the hydrogel comprises 2% w/v of graphene material.

3. The medical device according to claim 1, wherein the lateral size of graphene material varies between 2-4 µm.

4. The medical device according to claim 1, wherein the graphene material is obtained by the modified Hummers' method.

5. The medical device according to claim 1, wherein the incorporated graphene material is in powder form or in a water dispersion form.

6. The medical device according to claim 1, further comprising a second polymer, an antifouling agent, a surfactant agent, a biomolecule, an antiseptic agent, an anti-inflammatory agent, an antibiotic agent, a therapeutic agent, a pharmaceutical dye, peptides, endothelial factor, growth factor, or mixtures thereof.

7. The medical device according to claim 1, wherein the graphene material is bound to at least one of the following elements: a biomolecule, an antiseptic agent, an anti-inflammatory agent, an antibiotic agent, a therapeutic agent, a pharmaceutical dye, peptides, an endothelial factor, and a growth factor.

8. The medical device according to claim 1, further comprising tetraethylene glycol dimethacrylate as a cross-linking agent.

9. The medical device according to claim 1, wherein the medical device is selected from the group consisting of: a cartilage substitute, an intervertebral disc, a catheter, a vascular graft, a heart valve, a stent, an artificial kidney, an artificial lung, a ventricular assist device, a contact lenses, a keratoprosthesis, and a scaffold.

* * * * *